United States Patent
Dekel et al.

(10) Patent No.: US 10,575,907 B2
(45) Date of Patent: Mar. 3, 2020

(54) REGISTRATION WITH TRAJECTORY INFORMATION WITH SHAPE SENSING

(71) Applicant: Biosense Webster (Israel) Ltd., Yokneam (IL)

(72) Inventors: Zvi Dekel, Zichron Yaakov (IL); Akram Zoabi, Kfar Masser (IL); Yaniv Ben Zrihem, Binyamina (IL); Noam Rachli, Hadera (IL); Helen Volfson, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 507 days.

(21) Appl. No.: 15/629,044

(22) Filed: Jun. 21, 2017

(65) Prior Publication Data

US 2018/0368917 A1    Dec. 27, 2018

(51) Int. Cl.
| | |
|---|---|
| *A61B 5/00* | (2006.01) |
| *A61B 1/00* | (2006.01) |
| *A61B 34/20* | (2016.01) |
| *G06T 19/00* | (2011.01) |
| *A61B 1/267* | (2006.01) |
| *A61B 5/06* | (2006.01) |

(52) U.S. Cl.
CPC ............ *A61B 34/20* (2016.02); *A61B 1/0005* (2013.01); *A61B 1/2676* (2013.01); *A61B 5/065* (2013.01); *G06T 19/00* (2013.01); *A61B 2034/2061* (2016.02); *A61B 2034/2065* (2016.02)

(58) Field of Classification Search
CPC .................................. A61B 1/00; G06T 9/00
USPC ......................................................... 382/128
See application file for complete search history.

(56) References Cited

U.S. PATENT DOCUMENTS

| | | | |
|---|---|---|---|
| 2004/0097805 A1 | 5/2004 | Verard et al. | |
| 2006/0116575 A1* | 6/2006 | Willis | A61B 5/0422 600/434 |
| 2008/0118103 A1 | 5/2008 | Pescatore et al. | |
| 2008/0247621 A1 | 10/2008 | Zarkh et al. | |
| 2011/0065982 A1 | 3/2011 | Wibowo et al. | |
| 2011/0295267 A1 | 12/2011 | Tanner et al. | |
| 2012/0059220 A1 | 3/2012 | Holsing et al. | |
| 2013/0204124 A1 | 8/2013 | Duindam et al. | |

(Continued)

FOREIGN PATENT DOCUMENTS

| | | |
|---|---|---|
| WO | 2015061756 A1 | 4/2015 |
| WO | 2016191298 A1 | 12/2016 |

*Primary Examiner* — Abolfazl Tabatabai (57) ABSTRACT

A method and system for automatic landmark registration and registration using trajectory information and shape sensing during an endoscopic procedure, such as bronchoscopy, are described herein. A segmentation centerline of airways of a lung may be generated based on a pre-operative computed tomography (CT) image of the lung. Landmarks may be automatically detected on the segmentation centerline corresponding to bifurcations in the airways of the lung. A location data point cloud of locations of a catheter through the airways of the lung during navigation may be generated. A bounding volume of the airways of the lung may be generated and a bounding volume centerline may be detected. Landmarks may be detected on the bounding volume centerline for the same bifurcations. Then, the two sets of landmarks may be mapped as part of registration. The trajectory information with shape sensing may be used to provide non-rigid or fine registration.

20 Claims, 11 Drawing Sheets

(56) References Cited

U.S. PATENT DOCUMENTS

2013/0223702 A1 8/2013 Holsing et al.
2013/0303892 A1* 11/2013 Zhao .................... A61B 5/061
600/424

* cited by examiner

$$E = \frac{1}{2}K_L\sum_i \Delta L_i^2 \frac{1}{L_i} + \frac{1}{2}K_\alpha \sum_i \Delta\alpha_i^2 \left[\frac{\frac{1}{2}}{L_i} + \frac{\frac{1}{2}}{L_{i+1}}\right] + \frac{1}{2}K_\theta \sum_i \Delta\theta_i^2 \left[\frac{\frac{1}{3}}{L_i} + \frac{\frac{1}{3}}{L_{i+1}} + \frac{\frac{1}{3}}{L_{i+2}}\right]$$

Change in lengths | Change in bend angles | Change in twist angles

REGISTRATION WITH TRAJECTORY INFORMATION WITH SHAPE SENSING

BACKGROUND

In the general field of endoscopy, a variety of medical instruments have been developed for minimally invasive diagnosis and surgery that employ the insertion of a flexible conduit into a patient through which a camera, tool or other implement can be inserted and operated at the conduit's distal end that has been selectively positioned at a desired location within the patient. Many types of medical instruments operate in such a manner, including, for example, bronchoscopes, endoscopes, anoscopes, sigmoidoscopes, rhinolaryngoscopes and laryngoscopes. Herein, general terms for such a medical instrument, such as endoscope, catheter or biopsy tool, may be used interchangeably with specific examples of such an instrument, such as a bronchoscope.

Endoscopic medical instruments may be used in conjunction with a three-dimensional (3D) digital map of the targeted area of the body to provide the physician or operator with the visualization and information needed to properly conduct the diagnostic and/or therapeutic procedures. Bronchoscopy is a specific example of an invasive endoscopy procedure that involves the insertion of an endoscope (e.g., bronchoscope) into the lungs. Bronchoscopy is used by physicians for mediastinal inspection and treatment of the human respiratory system, such as the larynx, trachea and other airways of the lungs. For example, bronchoscopy may be used to locate a tumor, inflammation, bleeding, or foreign bodies in the airways.

SUMMARY

A method and system for automatic landmark registration and registration using trajectory information and shape sensing during an endoscopic procedure, such as bronchoscopy, are described herein. A segmentation centerline of airways of a lung may be generated based on a pre-operative computed tomography (CT) image of the lung. A first set of landmarks may be automatically detected on the segmentation centerline corresponding to bifurcations in the airways of the lung.

A catheter may be navigated through the airways of the lung and a location data point cloud including locations of the catheter during navigation may be generated. A bounding volume of the airways of the lung may be generated based on the location data point cloud, and a bounding volume centerline may be detected from the bounding volume of the airways. Then, a second set of landmarks in the airways may be detected on the bounding volume centerline, which corresponds to the first set of landmarks that were automatically detected on the segmentation centerline. Then, the two sets of landmarks may be mapped as part of registration.

The navigation of the catheter through the airways may use trajectory information with shape sensing to identify a distance of the catheter from a bifurcation in the airways of the lung to provide non-rigid or fine registration. An energy model may be generated based on lengths of positions of the catheter, bending angles of the catheter, and twisting angles of the catheter. A path may be selected that minimizes the energy value between the first set of landmarks and the set of landmarks to achieve more accurate registration.

DETAILED DESCRIPTION OF THE EMBODIMENTS

The disclosures are described herein with respect to bronchoscopy procedures for the respiratory and pulmonary system, although it is understood by one skilled in the art that the disclosures may be applied to systems and procedures that can be used in any cavity or system in the body, including, but not limited to, the respiratory/pulmonary system, the cardiac system, the digestive system, the neurovascular system, and/or the circulatory system.

Navigated bronchoscopy typically involves the insertion of a navigation catheter (e.g., a bronchoscope), which may act as viewing instrument, into the airways by a physician (e.g., via the mouth or other opening or incision). For example, a bronchoscope may be mounted with a camera and/or electromagnetic (EM) sensor to capture video, images and/or sensor data of the position of the catheter as it passes through lung pathways. The catheter may have other functions as well, including, but not limited to the following: being equipped with electrodes that may be used to perform therapeutic ablation on defective tissue; being equipped with optical sensors; and/or being equipped with temperature sensors.

Flexible or rigid bronchoscopy may be used. A rigid bronchoscope is a straight tube and is used in larger airways to remove large amounts of blood, secretion, foreign objects or diseased tissue (lesions), to control bleeding, or to insert stents, for example. A flexible bronchoscope can be moved into smaller airways (e.g., bronchioles) and may be used to insert breathing tubes to provide oxygen, suction out secretion, perform biopsies, and deliver medicine into the lungs, for example.

Figure 1:
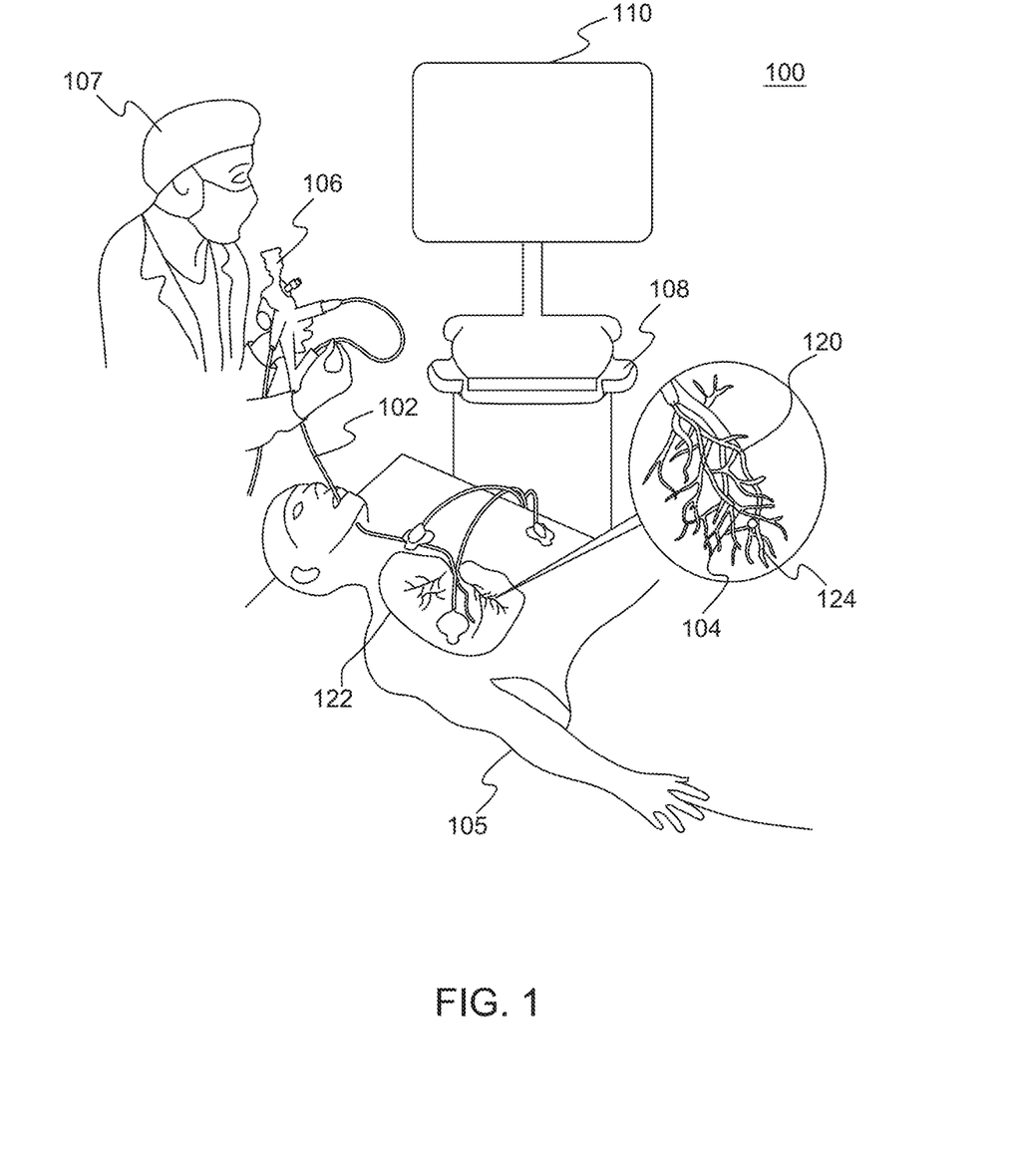
FIG. 1 is a system diagram of an example flexible bronchoscopy system.

FIG. 1 is a system diagram of an example flexible bronchoscopy system 100, in accordance with the disclosure herein. The example bronchoscopy system 100 includes a flexible conduit 102 which has a distal end 104 where a camera or sensor and associated light emitter may be disposed.

The example bronchoscopy system 100 may include a robotic handle 106 and associated controller 108 and video display 110 that enable a physician or other operator 107 to selectively and precisely insert the distal end 104 of the flexible conduit 102 to a desired location within the air passages 120 of the lungs 122 of a patient 105. For example, FIG. 1 illustrates the result of the insertion of the flexible conduit 102 to locate the distal end 104 of the flexible conduit 102 proximate to a tumor 124.

The display 110 may be configured to display images from the camera or sensor of the distal end 104, which may be combined with pre-operative computed tomography (CT) images (and/or magnetic resonance imaging (MRI) images), to assist the physician 107 in navigating through the air passages 120 while inserting the flexible conduit 102 to reach the desired location using the robotic handle 106. The robotic handle 106 may be controlled, at least in part, by the controller 108 to effectuate the insertion movement directed by the physician 107.

The flexible conduit 102 may include optic fiber(s) (e.g., embedded lengthwise along the conduit 102) which may be part of the signaling components for the camera, sensor or light emitter of the distal end 104. The controller 108 may be configured with fiber optic sensing to generate data via the optic fiber(s) to assist in the control of the flexible conduit 102 and the display of a representation of the conduit location within the patient's airways 120 as a portion of displayed graphics on the display 110 during use. The fiber optic sensing performed by the controller 108 may provide precise calculations of the path and curvature of the conduit 102 in situ during a bronchoscopic procedure.

The controller 108 may include, but is not limited to include, any one or more of the following elements (not specifically shown): a processor; a storage medium; and/or an operator interface. For example, the controller 108 may include one or more signal processing circuits that may be contained inside a computer. The controller 108 may be implemented in hardware and/or programmed in software to carry out the functions of the bronchoscopy system 100. This software may be downloaded to the controller 108 in electronic form, over a network, for example, and/or it may be provided on tangible media, such as magnetic or optical media or other nonvolatile memory. For example, enhancement may be made to bronchoscopy system 100 by downloading and installing software modules to the controller 108 (e.g., processor and/or storage medium). In an example, controller 108 may comprise a general-purpose computer.

In navigated image-based bronchoscopy systems, such as the bronchoscopy system 100 shown in FIG. 1, physicians manually navigate a catheter (e.g., bronchoscope, biopsy tool, etc.) within the lung, and thus depend upon the visualization of the surrounding anatomy to successfully navigate the lung and perform bronchoscopic procedures. The position of the bronchoscope and/or biopsy tools may be tracked and displayed in real-time in a visually displayed three-dimensional (3D) map of the patient's lung, thus providing the operator with an endobronchial pathway towards a predefined target (e.g., a tumor or lesion).

To generate the 3D map of the lungs in advance of the bronchoscopy procedure, preoperative two-dimensional (2D) CT images (MRI images may alternatively or additionally be used) of the patient's lungs may be taken from different angles and combined using digital processing to create a single 3D view of the patient's lung, including the complex structure of the airway tree. This process is referred to as medical image segmentation and is commonly used in medical imaging to create 3D reconstructions from 2D images by isolating and extracting anatomical structures of interest (in this case, in the airways) from the preoperative images.

Airway segmentation is particularly challenging because of the complex structure of the airways, and the very small diameters of some of the bronchi (e.g., bronchioles can be less than 1 millimeter (mm) in diameter) making it difficult to distinguish them on a CT (or MRI) image. An example technique for airway segmentation involves the identification of three (or more) seed points or landmarks on the CT (or MRI) image: for example, within the trachea and each of the two main bronchi. The landmarks may be used to split the volume into three different parts to be used as starting points for three segmentation processes.

Figure 2:
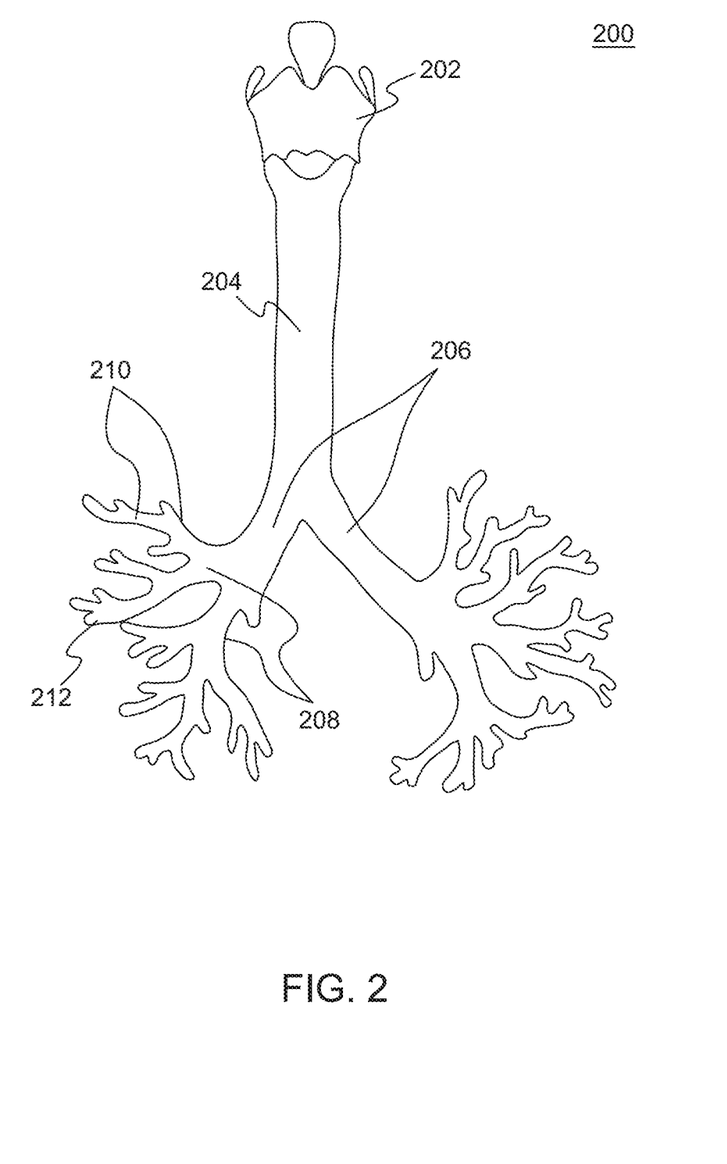
FIG. 2 is an example illustration of the lung anatomy showing the pathways in the lung that may be relevant for navigation during bronchoscopy.

FIG. 2 is an example illustration of the lung anatomy 200 showing the pathways in the lung that may be relevant for navigation during bronchoscopy. For example, a map of the lung generated by airway segmentation may show, but is not limited to show, the following elements of the lung anatomy 200: the larynx 202; the trachea 204; the primary bronchi 206; the secondary bronchi 208; the tertiary bronchi 210; and/or the bronchioles 212. Other elements, not shown, may be included in a map of the lung including, but not limited to, the following: the pulmonary artery, pulmonary veins, and/or the right and left lung.

Once a 3D map of the lung is generated, image-to-patient registration may be used to accurately align the path of navigation of the catheter in the patient to the 3D map of the lung. Generally, image registration is the process of transforming different sets of data points into one coordinate system, and is used in medical imaging to integrate the data points obtained from the different sources of location data points, and can be used for 2D and 3D images. A goal of image registration is to bring corresponding points of the two images as close as possible. Image registration for medical imaging typically has to account for movement of the anatomical region of the body, and thus multiple images may be taken and transformed into a single fixed image of the anatomical region.

In bronchoscopy, or endoscopy in general, image registration serves to map the image of the airways (or other organ) from the inside, using a catheter, to the images from a CT scan. Registration may be achieved by performing a geometric transformation to map between the coordinate system X used for navigation of the catheter (e.g., the target image) and the coordinate system Y used for the CT (or MRI) scans in segmentation (e.g., the reference image). For example, if the point x in the coordinate system X corresponds to the point y in coordinate system Y, then a successful registration will make transformed point $x'=T(x)$ equal or approximately equal to y, where T is the transformation function applied to the point x.

An example of image-to-patient registration is centerline-based registration, where the position data from the bronchoscope (catheter) tip as it navigates the pathway (e.g., trachea and bronchi) through the airways is matched to the path (i.e., centerline) of the lumen (i.e., inside space) in the trachea bronchi of the patient's lungs from the preoperative CT images. Registration may include "rigid" registration, which involves matching pairs of points between the coordinate system of the CT images and the coordinate system of the physical world (e.g., magnetic coordinate system used by the catheter) using linear transformations, which may include rotation, scaling, and/or translation.

The linear transformations used in rigid registrations may not be able to model all local geometric differences between the images. Thus, elastic or non-rigid registration (also called fine registration) may also be used which may involve the use of transformations that are capable of warping the target image to align with the reference image. Non-rigid registration is particularly useful for obtaining and matching accurate location information in the small distal airways of the lungs, such as the tertiary bronchi and the bronchioles.

In an example, as part of rigid registration, an iterative closest point (ICP) algorithm, that matches points in a source point cloud to the closest corresponding points in a reference point cloud, may be used to map the path of the tracked bronchoscope (e.g., a catheter location point cloud) to the centerline of the lung tree identified in segmentation. In this case, the ICP algorithm may make use of key points of reference or landmarks (i.e., seed points) along the airway centerline, which may be generated by a preliminary point set landmark registration process.

Currently, the segmentation and registration process for bronchoscopy is only semi-automated, but not fully automated, because landmark selection (i.e., seed point placement within the trachea and bronchi) is done manually by the physician or operator, which is time consuming, costly and vulnerable to human error. Thus, there is a need by physicians for an accurate and automatic registration process in which, by quickly visiting the trachea and the left and right main (primary) bronchi with the catheter, the bronchoscopy system may obtain an accurate registration between the navigation coordinate system and the CT coordinate system in order to further navigate to the distal bronchi (e.g., secondary and tertiary bronchi and bronchioles) over the CT image and its segmentation result.

Figure 3:
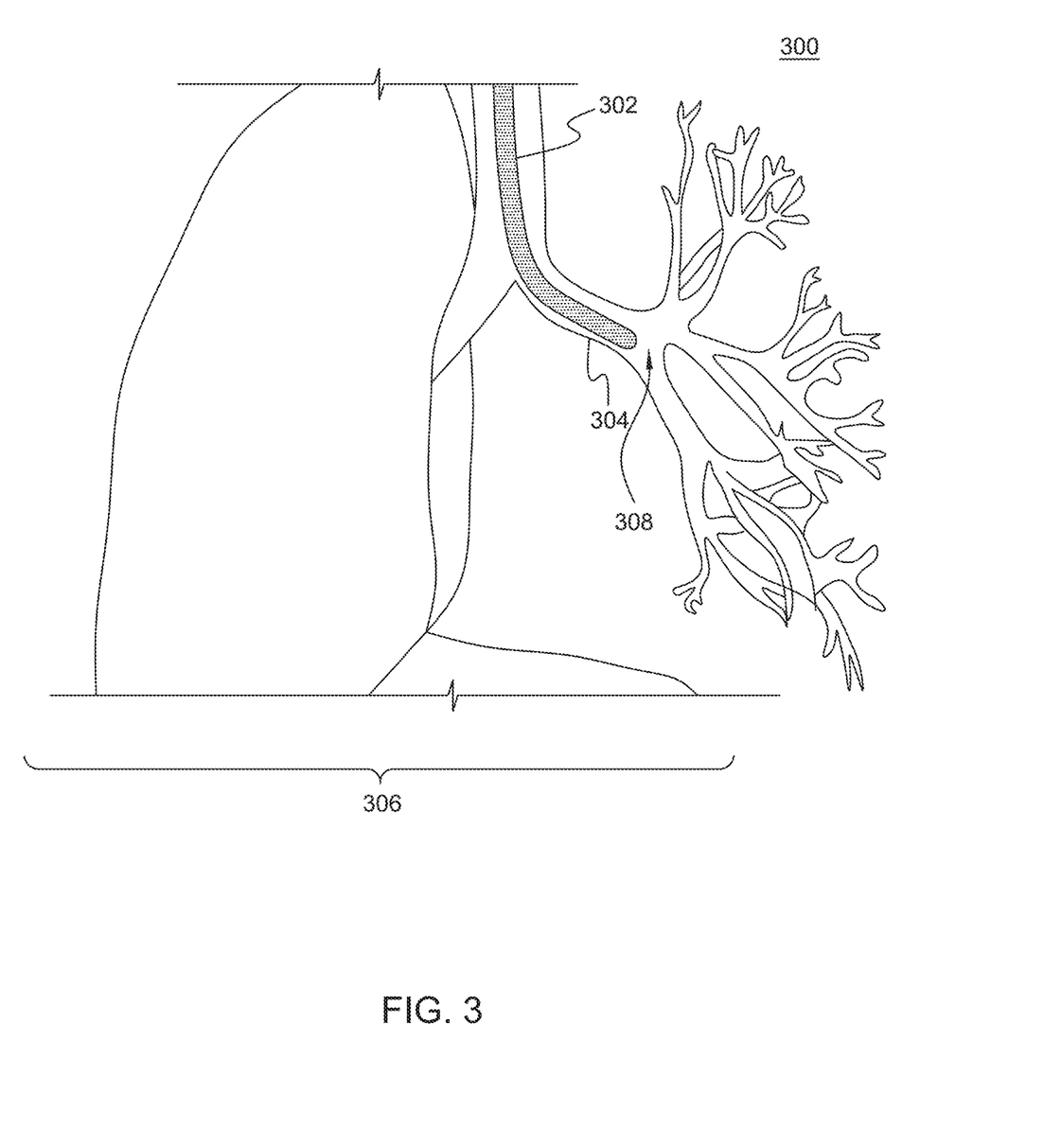
FIG. 3 is an example procedure cross-sectional view of the path of a catheter in the airways of the lungs as part of an automatic detection and registration of anatomical landmarks process.

The disclosed bronchoscopy system uses the navigation information from the catheter to automatically detect anatomical landmarks within the lung to provide better navigation information. FIG. 3 is an example cross-sectional view 300 of the path of a catheter 302 in the airways of the lungs 306 as part of an automatic detection and registration of anatomical landmarks process, in accordance with the disclosures herein. In the example image 300, the catheter 302 is navigated through the main airway 304 of the lungs 306. When the catheter 302 arrives at a "T" junction or bifurcation 308 in the main airway, the registration process automatically detects the structure of the airway and updates the registration by marking an automatically detected bifurcation 308 as a landmark. The disclosed bronchoscopy system using automatic detection and registration of anatomical landmarks is described in further detail below.

Figure 4A:
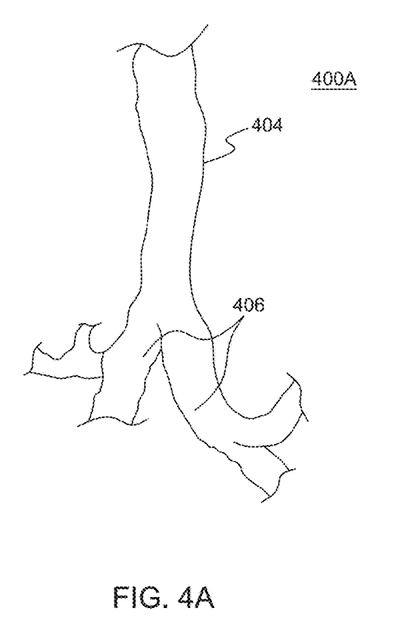
FIG. 4A is an image of an example reconstruction of the main airways of the lungs and FIG. 4B is a corresponding skeletonized image of the centerline of the main airways of the lungs.
Figure 4B:
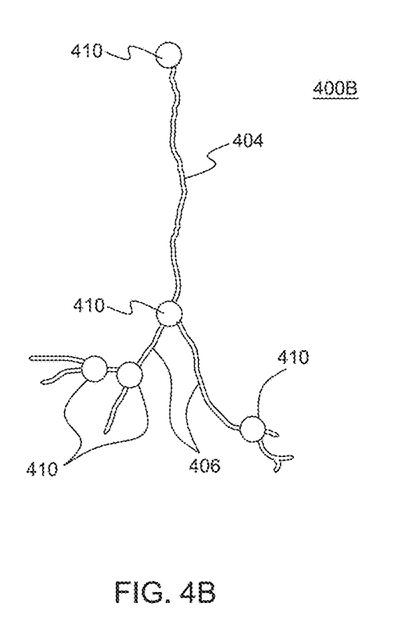

In accordance with the disclosure herein, as part of the registration process, the disclosed bronchoscopy system may collect the catheter locations using multiple sensors or fiber optics, located in the catheter, while the physician maneuvers the catheter within the main airway segments. Using the gathered location points during catheter navigation, the disclosed bronchoscopy system may automatically reconstruct the trajectory of the main airways and may automatically skeletonize the trajectory centerline. The disclosed bronchoscopy system may then detect all of centerline junctions of the main airways by identifying each split (corresponding to a bifurcation) in the centerline and define the locations of the splits as candidates for landmarks. FIG. 4A shows an image of an example reconstruction 400A of the main airways of the lungs, including the trachea 404 and the left and right primary bronchi 406, and FIG. 4B shows a corresponding skeletonized image 400B of the centerline of the main airways of the lungs, including the trachea 404 and the left and right primary bronchi 406, and showing the automatically detected proximal bifurcations or landmarks 410 at the junctions of the airways where there are splits in the centerline.

The disclosed bronchoscopy system may also segment the CT (or MRI) image of the main airways of the lungs acquired prior to bronchoscopy and skeletonize the centerline of the CT image while automatically detecting the main airway junctions. Thus, the disclosed bronchoscopy system may generate two sets of centerline junction locations of the main airways of the lungs, based on the navigation process using the catheter and the preoperative CT scan, respectively. The disclosed bronchoscopy system may then perform point set registration between the two sets of centerline junction locations, as described below.

For example, the disclosed bronchoscopy system may perform ICP registration between the trajectory points (i.e., set of points identifying junctions along the centerline) constructed during navigation and the trajectory points constructed during airway segmentation (i.e., based on CT scan) starting from the point set registration results. In an example, the disclosed bronchoscopy system may optimize the registration results by the ICP process using a linear programming algorithm, such as the simplex algorithm.

The disclosed bronchoscopy system enhances current registration systems by automatically detecting and registering the landmarks within the lung used for image registration to provide better navigation information. The disclosed system eliminates the need for initial registration by user, and prevents human error in selecting landmarks (e.g., bifurcations or junctions in the airways).

Figure 5:
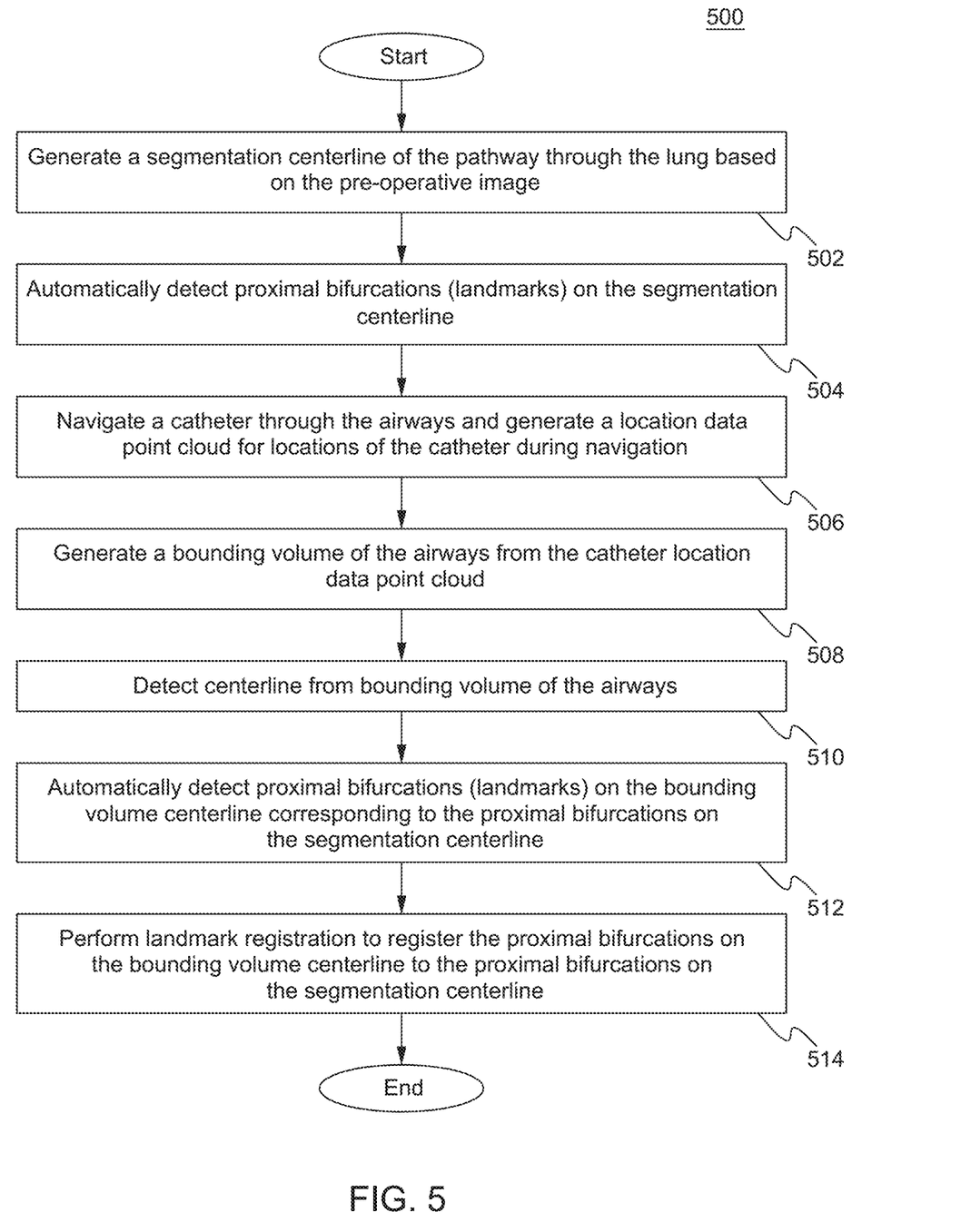
FIG. 5 is a flow diagram of an example automatic landmark registration procedure for use in a bronchoscopy system, in accordance with the disclosures herein.

FIG. 5 is a flow diagram of an example automatic landmark registration procedure 500 for use in a bronchoscopy system, in accordance with the disclosures herein. In the automatic landmark registration procedure 500, centerline-based registration is used to align the CT images with the pathway of the bronchoscope; however, other registration techniques may be similarly used.

At 502, a segmentation centerline of the pathway through the lung may be generated based on the CT image (and/or an MRI image). The segmentation centerline may be generated using any method for centerline extraction. For example, a thinning algorithm may be applied to the surface model of the airways from the CT scan images.

At 504, proximal bifurcations (landmarks) are automatically detected on the segmentation centerline. For example, with reference to FIG. 4B, four proximal bifurcations 410 are detected. Due to the anatomy of the lung, preferably three or more landmarks are detected at major junctions, such as the junctions between the trachea and the primary bronchi, and the junctions between the primary bronchi and the secondary bronchi. Landmarks from the CT scan may be detected as hierarchical splits in the centerline (as shown in FIG. 4B).

At 506, a catheter is navigated through the airways and a location data point cloud is generated for the locations of the catheter during navigation. For example, the catheter may pass through the main pathways (e.g., trachea, primary bronchi, secondary bronchi) of the lungs to generate a location data point cloud by recording the locations of the catheter during navigation (e.g., by determining location, orientation and/or distance of the distal tip of the catheter relative to a reference device constellation located beneath the body). At 508, the surface geometry of the airways may be detected to generate a bounding volume of the airways from the location data point cloud of where the catheter has been (i.e., the 3D catheter location point cloud including all catheter positions). For example, an anatomy mapping algorithm, such as an alpha volume algorithm, may generate the chamber geometry of the airways from the location data point cloud.

At 510, the centerline from the bounding volume of the airways may be detected (e.g., using thinning algorithms). At 512, proximal bifurcations (e.g., three or more) may be automatically detected on the bounding volume centerline that correspond to the proximal bifurcations on the segmentation centerline from step 504. The landmarks from the catheter's positions may be detected by detecting splits in the bounding volume centerline.

Figure 6A:
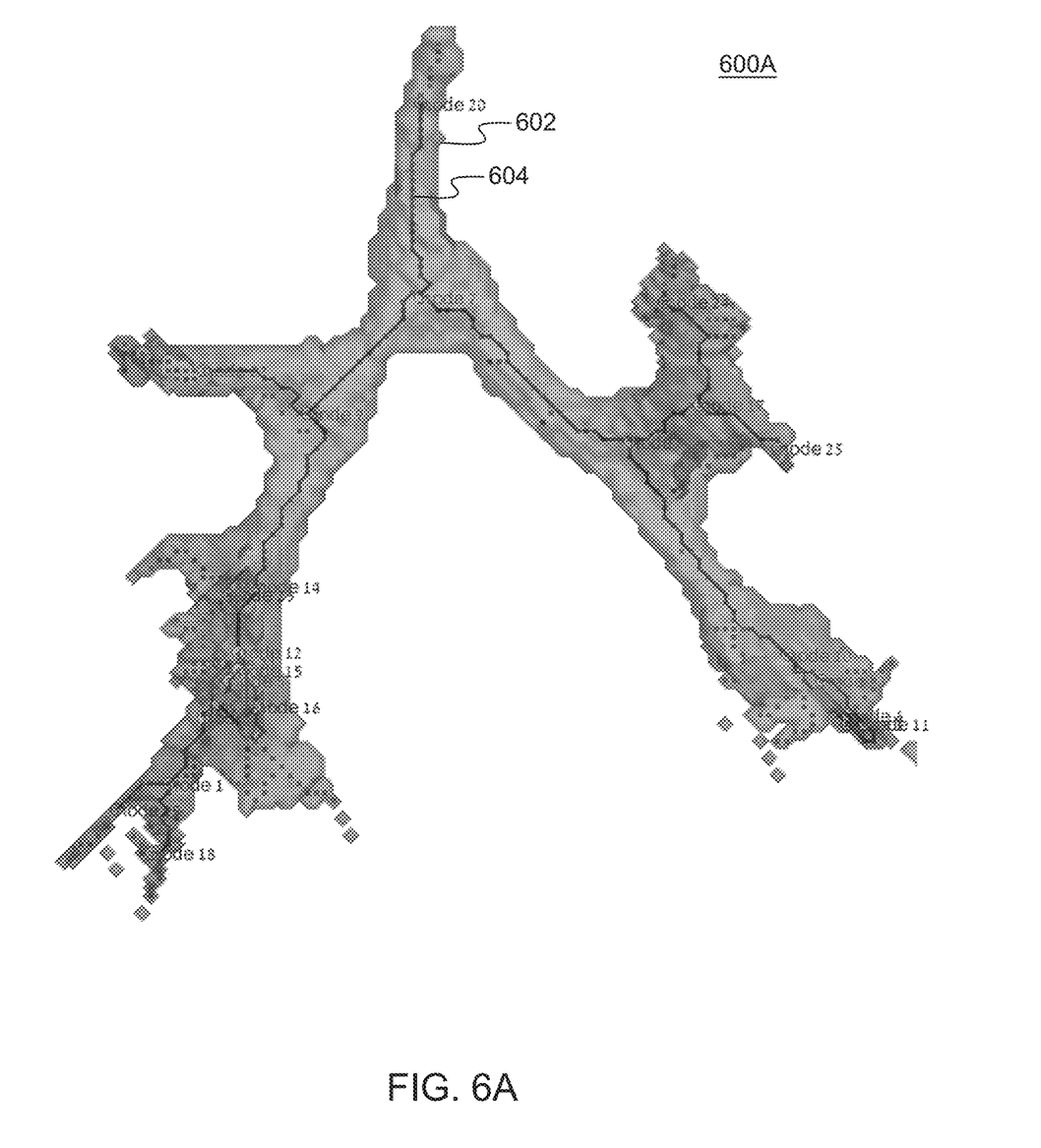
FIG. 6A is a graph of the segmentation of the airways volume and the centerline that is automatically extracted from the airways volume.
Figure 6B:
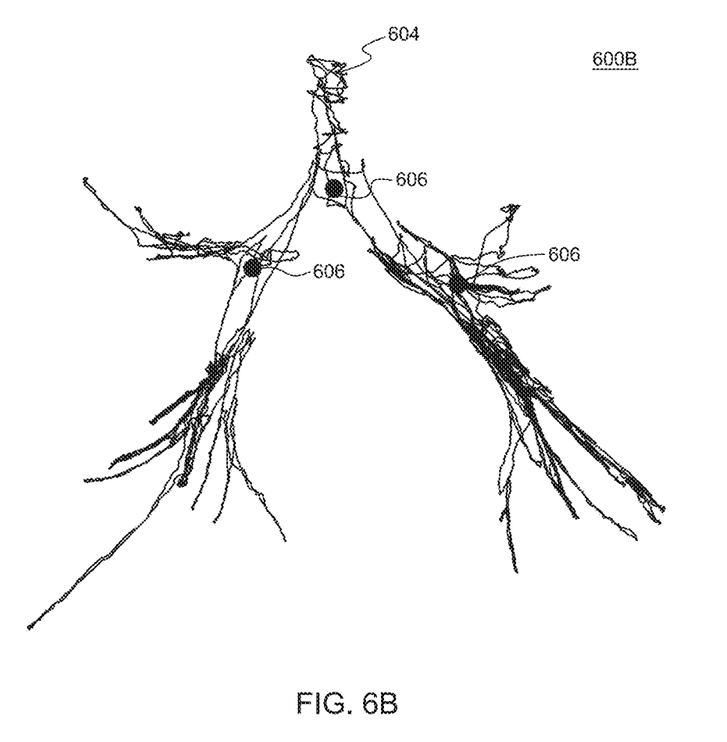
FIG. 6B is a graph of the extracted centerline showing the results of the automatic landmark detection that identifies the landmarks at bifurcation points on the centerline.

FIGS. 6A and 6B show graphs 600A and 600B of an example airway centerline 604 with identified bifurcations points using automatic landmark detection. In particular, FIG. 6A is a graph 600A of the segmentation of the airways volume 602, shown in gray, and the centerline 604 that is automatically extracted from the airways volume 602, shown as a black line. The centerline 604 corresponds to the path of the catheter (not shown). The nodes labeled on the graph (e.g., node 1, node 2, etc.) are candidate landmarks detected from the CT scan, such that any subset (or all) of the detected candidate landmarks may be selected as landmarks for use in landmark registration (step 514, described below). FIG. 6B is a graph 600B of the extracted centerline 604 showing the result of the automatic landmark detection that automatically identifies landmarks 606, represented by black circles, at bifurcation points (e.g., splits) on the centerline 604. In this example, the landmarks 606 are identified between the trachea and primary bronchi, and between the primary bronchi and secondary bronchi. FIG. 6B shows three detected landmarks 606, however any number of landmarks may be identified.

Referring back to FIG. 5, at 514, a landmark registration procedure may be performed to map the proximal bifurcation points on the bounding alpha volume centerline to the proximal bifurcation points on the segmentation centerline, thus providing the necessary correspondence between the map of the lung generated by the CT scan and the path of the catheter in the lung in order to achieve accurate navigation during bronchoscopy. In an example, a singular value decomposition (SVD) algorithm may be used to map the two sets of points.

In order to pair between landmarks from the CT image and from the catheter's position, different anatomical features may be compared. For example, the first bifurcation or split from the trachea may be defined in both sets of points as the main split. The distances between the main split to secondary splits (e.g., between the primary and secondary bronchi) may be compared between the two sets of points. The angle between the main split and the secondary splits may also be compared. This process may be repeated, for example, from the secondary splits to tertiary splits (e.g., between secondary bronchi and tertiary bronchi), and so on an so forth.

Another challenge with image-to-patient registration is that the accuracy of fine or non-rigid registration decreases as the distal end of the catheter enters the small distal airways, such as the tertiary bronchi and the bronchioles, which cause inaccuracy in determining the exact position (location) of the catheter in the airways. Currently, physicians manually navigate catheters within the lung, which may need detailed and accurate visualization of the surrounding anatomy, including in the distal airways, for example if it is the location of a tumor.

As described above, the image registration process transforms different sets of data into one coordinate system. For bronchoscopy, the first set of data location points is for the location of catheter tip as it navigates the airways (acquired for example by an electromagnetic navigation system) and the second set of location data points is for the image of the bronchial (e.g., based on the CT images). For example, image registration may map certain areas of the lung, such as the trachea and bronchi. The disclosures herein provide an improved registration process and system for non-rigid registration that utilizes trajectory information with shape sensing to provide more precise registration for navigation within the lung, particularly in the small distal airways where it is difficult to obtain accurate catheter location information.

The disclosed registration system and process provides an improvement to existing registration systems by tracking the trajectory of the catheter using multiple sensors or fiber optics in the catheter for shape sensing. Shape sensing involves the use of continuous fiber optic (optical) shape sensors, based on a distributed Bragg reflector (DBR) (e.g., a Fiber Bragg Gratings (FBG)), in the catheter, to aid in navigating and positioning the catheter that can sense in a spatially continuous manner, providing information about the location of the entire length of the catheter. The bronchoscopy system may compare the actual shape of the airway using shape sensing to the trajectory of the catheter to obtain more accurate registration. Using this method, the system and method can compensate for the movements of the airways (e.g., due to movement of the anatomy caused by breathing etc.) and also deformation of the airways in the real world versus the shape of the airways in the CT image due to mechanical stress imposed by the catheters or bronchoscope.

Figure 7:
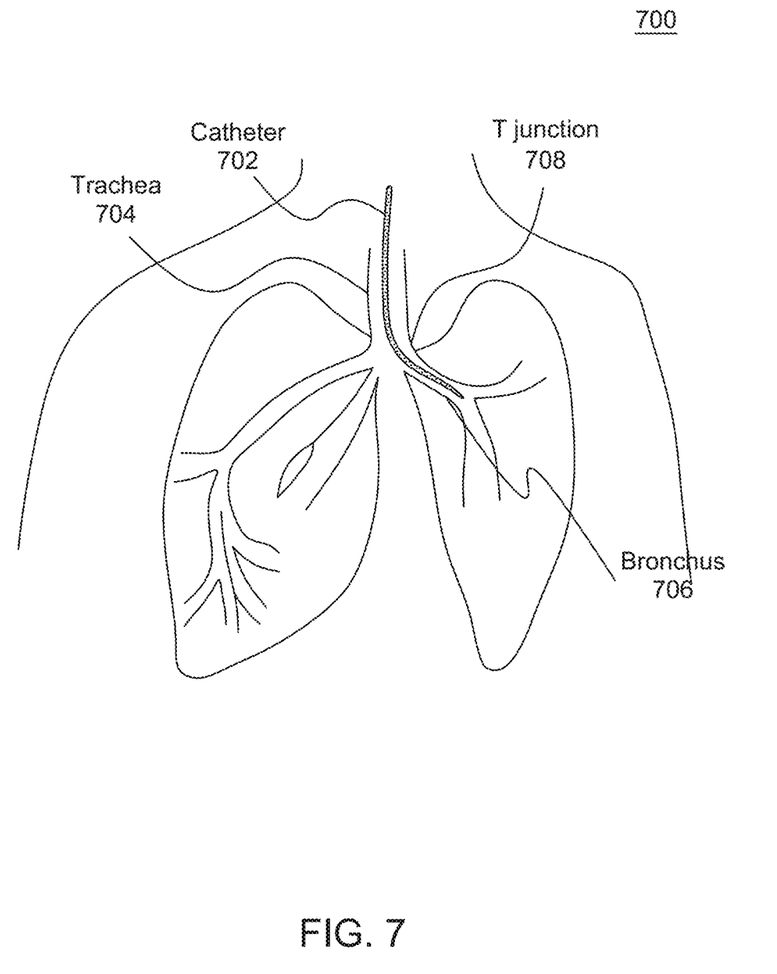
FIG. 7 is an example image of the lung anatomy showing the path of a catheter in the airways of the lungs as part of an improved fine (non-rigid) registration process using trajectory information and shape sensing.

FIG. 7 is an example image of the lung anatomy 700 showing the path of a catheter 702 in the airways of the lungs as part of an improved fine (non-rigid) registration process using trajectory information and shape sensing, in accordance with the disclosures herein. When the physician navigates a catheter 702 within an airway, such as the trachea 704, and the catheter 702 approaches a T junction or bifurcation in the airways, such as the T junction 708 from trachea 704 to bronchus 706, the physician may utilize trajectory information with shape sensing to identify the distance of the catheter 702 from the T junction 708. More specifically, when the catheter 702 arrives at the junction 708, the registration of the path of the catheter 702 may be updated using trajectory information and shape sensing is used to improve the mapping and display of the anatomy of the lung pathways.

The disclosed registration system and process includes tracking the trajectory of the catheter using multiple sensors or fiber optics with shape sensing to improve the mapping and display of the anatomy of the lung pathways. The path of the magnetic positions of the catheter during navigation may be used in order to refine the translation and/or the rotation of the registration process. That is, knowing the path of the catheter, instead of only the position of the tip of the catheter, allows the disclosed registration system to identify accurate position information by eliminating anatomies that are impossible in comparison to the path of the catheter.

Figure 8:
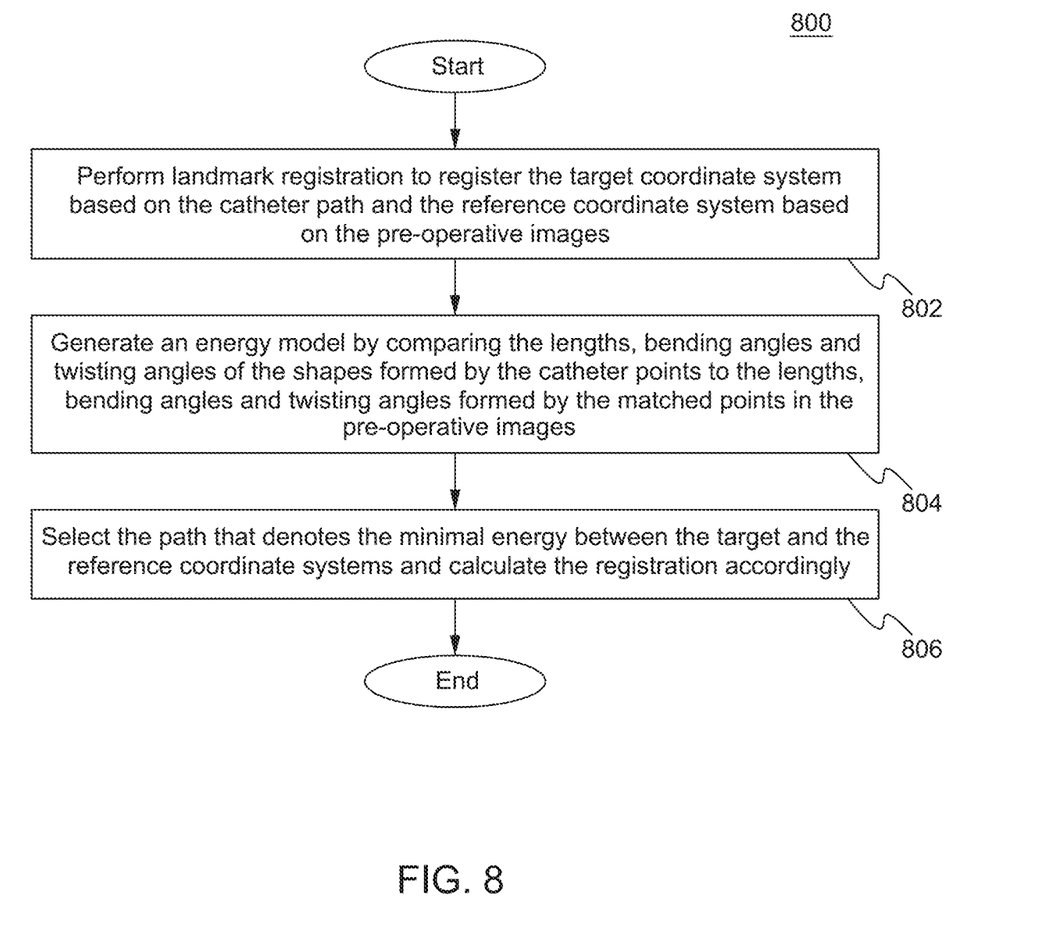
FIG. 8 is a flow diagram of an example registration procedure using trajectory information for use in a bronchoscopy system.

FIG. 8 is a flow diagram of an example registration procedure 800 using trajectory information for use in a bronchoscopy system, in accordance with the disclosures herein. At 802, landmark registration is performed to register the target coordinate system based on the catheter path and the reference coordinate system based on the CT images, for example using any of the techniques described above (e.g., automatic landmark registration procedure 500 in FIG. 5). In an example, an ICP algorithm may be used to improve the rigid registration.

At 804, an energy model may be generated. The energy model may be defined by comparing the lengths, bending angles and twisting angles of the shapes formed by the catheter points to the lengths, bending angles and twisting angles formed by the matched points in the pre-operative images. The lengths, bending angles and twisting angles my may first be calculated separately for each point set (i.e., the catheter point set and the matched points from the pre-operative images).

Figure 9:
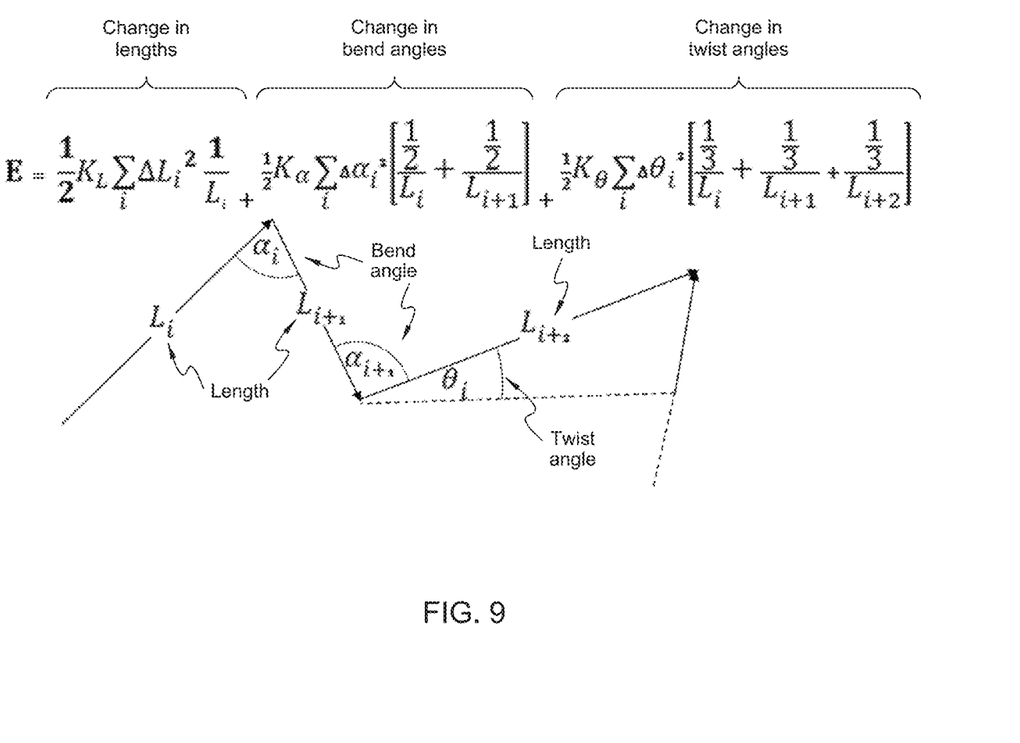
FIG. 9 is an illustration of the elements of the energy model including the length portion, the bending portion and the twisting portion.

FIG. 9 is an illustration of the elements of the energy model including the length portion, the bending portion and the twisting portion, in accordance with the disclosures herein. With reference to FIG. 9 and Equation 1, if P denotes the set of location points in either the target coordinate system (based on catheter location) or the reference coordinate system (based on pre-operative CT or MRI images), then the vector from each point in P to the consequent point in P along the path may be denoted by DP. The lengths ΔL may be defined as the distances between any two consequent (i.e., consecutive) points in P along the path. The bending angles, denoted by α, may be defined as the angles between two consequent DP vectors. Two consequent DP vectors define a plane, and the twisting angles, denoted by θ, may be defined as the angles between two consequent planes.

Thus, the energy E representing the changes in lengths, bend angles and twist angles in a catheter path may be defined by Equation 1:

$$E = \frac{1}{2}K_L \sum_i \Delta L_i^2 \frac{1}{L_i} + \frac{1}{2}K_\alpha \sum_i \Delta \alpha_i^2 \left[\frac{1/2}{L_i} + \frac{1/2}{L_{i+1}}\right] + \frac{1}{2}K_\theta \sum_i \Delta \theta_i^2 \left[\frac{1/3}{L_i} + \frac{1/3}{L_{i+1}} + \frac{1/3}{L_{i+2}}\right]$$ Equation 1 where $K_L$ is the elastic stretching coefficient; $\Delta L_i^2$ is the change in length between the magnetic path and match path; $K_\alpha$ is the elastic bending coefficient; $\Delta \alpha_i^2$ is the change in angle between two consecutive sections of the magnetic path and match path; $K_\theta$ is the elastic twisting coefficient; $\Delta \theta_i^2$ is the change in twist angle between three consecutive sections of the magnetic path and match path; and $L_i$, $L_{i+1}$ and $L_{i+2}$ are the length of sections over the length of path used for energy calculations.

With reference to FIG. 8, at 806, the path that denotes the minimal energy E (e.g., using Equation 1) between the target (catheter navigation) coordinate system and the reference (CT scan based) coordinate systems is selected and the registration is calculated accordingly.

Figure 10:
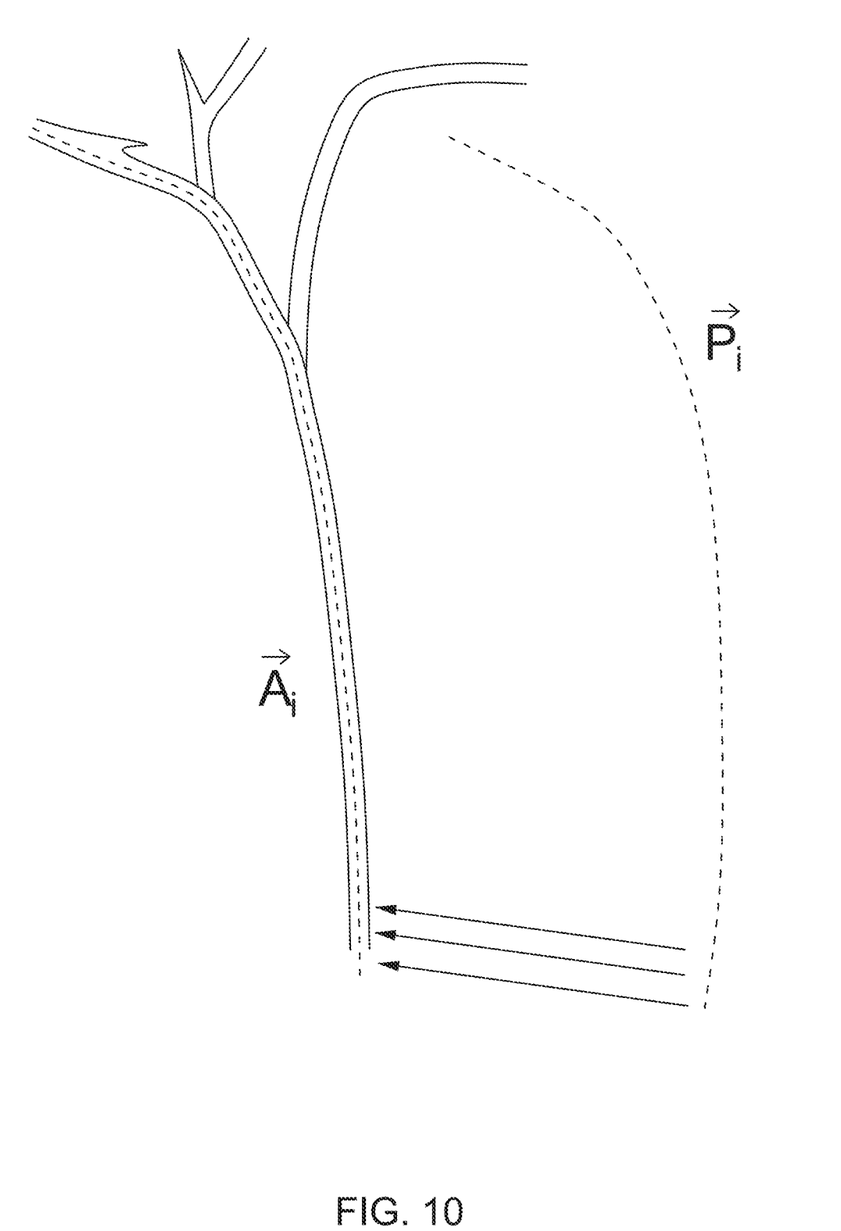
FIG. 10 is an example of the catheter path $\vec{P}_i$ before registration and the matched catheter path $\vec{A}_i$ after registration.

FIG. 10 is an example of the catheter path $\vec{P_i}$ before registration and the matched catheter path $\vec{A_i}$ after registration, such that the matched path $\vec{A_i}$ is the path that minimizes the energy value E of changing the catheter path.

The embodiments and procedures described herein may be implemented in hardware, and/or software. A computer system for performing ablation may be capable of running software modules that introduce additional features including the procedures described herein. The procedures described herein may enable advanced cardiac visualization, and diagnostic capabilities to enhance clinicians' ability to diagnose and treat heart rhythm disorders. Although the procedures disclosed herein are describe with respect to ablation procedures within the heart, the procedures may be similarly used for ablation in other parts of the body.

What is claimed is:

1. A method for automatic landmark registration during a bronchoscopy procedure, the method comprising:
   generating a map of airways of a lung based on a pre-operative image of the lung, wherein the map can be displayed on a visual display;
   generating a segmentation centerline of the airways of the lung based on the pre-operative image of the lung;
   automatically detecting a first plurality of landmarks on the segmentation centerline, wherein the first plurality of landmarks correspond to bifurcations in the airways of the lung;
   generating a location data point cloud based on locations of a catheter during navigation through the airways of the lung;
   generating a bounding volume of the airways of the lung based on the location data point cloud;
   detecting a bounding volume centerline from the bounding volume of the airways of the lung;
   automatically detecting a second plurality of landmarks on the bounding volume centerline corresponding to the bifurcations of the first plurality of landmarks; and
   generating a mapping of the first plurality of landmarks to corresponding points in the second plurality of landmarks and using the mapping to integrate the location data point cloud with the map of the airways of the lung.

2. The method of claim 1, further comprising:
   using the mapping to visually display in real-time the locations of the catheter during navigation in the airways of the lungs on the map of the airways of the lung.

3. The method of claim 2 wherein the map of the airways of the lung is visually displayed as a two-dimensional (2D) or three-dimensional (3D) image.

4. The method of claim 1, wherein the plurality of landmarks includes three or more landmarks.

5. The method of claim 1, wherein the automatically detecting the first plurality of landmarks on the segmentation centerline and the automatically detecting the second plurality of landmarks on the bounding volume centerline includes identifying splits in the segmentation centerline and the bounding volume centerline, respectively.

6. The method of claim 1, wherein the bifurcations in the airways of the lung include: a first T junction between a trachea of the lung and at least one bronchus of the lung, and a second T junction between a first bronchus of the lung and a second bronchus of the lung.

7. The method of claim 1, wherein the generating the mapping uses singular value decomposition (SVD).

8. The method of claim 1, wherein the pre-operative image of the lung is generated using computed tomography (CT) or magnetic resonance imaging (MRI).

9. The method of claim 1, wherein the navigating the catheter through the airways of the lung includes:
   using trajectory information with shape sensing to identify a distance of the catheter from a T junction in the airways of the lung.

10. The method of claim 9, wherein the shape sensing includes:

calculating an energy value by comparing lengths, bending angles, and twisting angles of shapes formed by the locations of the catheter during navigation to lengths, bending angles, and twisting angles of matched points in the pre-operative image; and selecting a path that minimizes the energy value.

11. A bronchoscopy system configured to perform automatic landmark registration during a bronchoscopy procedure, the bronchoscopy system comprising:

a processor operatively coupled to a catheter and a visual display device;

the processor configured to generate a map of airways of a lung based on a pre-operative image of the lung, wherein the map can be displayed on a visual display;

the processor configured to generate a segmentation centerline of the airways of the lung based on the pre-operative image of the lung;

the processor configured to automatically detect a first plurality of landmarks on the segmentation centerline, wherein the first plurality of landmarks correspond to bifurcations in the airways of the lung;

the processor configured to generate a location data point cloud based on locations of the catheter during navigation through the airways of the lung;

the processor configured to generate a bounding volume of the airways of the lung based on the location data point cloud;

the processor configured to detect a bounding volume centerline from the bounding volume of the airways of the lung;

the processor configured to automatically detect a second plurality of landmarks on the bounding volume centerline corresponding to the bifurcations of the first plurality of landmarks; and the processor configured to generate a mapping of the first plurality of landmarks to corresponding points in the second plurality of landmarks and use the mapping to integrate the location data point cloud with the map of the airways of the lung.

12. The bronchoscopy system of claim 11, wherein the visual display is configured to use the mapping to visually display in real-time the locations of the catheter during navigation in the airways of the lungs on the map of the airways of the lung.

13. The bronchoscopy system of claim 12, wherein the visual display displays the map of the airways of the lung as a two-dimensional (2D) or three-dimensional (3D) image.

14. The bronchoscopy system of claim 11, wherein the plurality of landmarks includes three or more landmarks.

15. The bronchoscopy system of claim 11, wherein the processor is configured to automatically detect the first plurality of landmarks on the segmentation centerline and automatically detect the second plurality of landmarks on the bounding volume centerline by identifying splits in the segmentation centerline and the bounding volume centerline, respectively.

16. The bronchoscopy system of claim 11, wherein the bifurcations in the airways of the lung include: a first T junction between a trachea of the lung and at least one bronchus of the lung, and a second T junction between a first bronchus of the lung and a second bronchus of the lung.

17. The bronchoscopy system of claim 11, wherein the processor is configured to generate the mapping uses singular value decomposition (SVD).

18. The bronchoscopy system of claim 11, wherein the pre-operative image of the lung is generated using computed tomography (CT) or magnetic resonance imaging (MRI).

19. The bronchoscopy system of claim 11, wherein the navigation of the catheter through the airways of the lung includes the processor using trajectory information with shape sensing to identify a distance of the catheter from a T junction in the airways of the lung.

20. The bronchoscopy system of claim 19, wherein the processor performs shape sensing by calculating an energy value by comparing lengths, bending angles, and twisting angles of shapes formed by the locations of the catheter during navigation to lengths, bending angles, and twisting angles of matched points in the pre-operative image and selecting a path that minimizes the energy value.

* * * * *

UNITED STATES PATENT AND TRADEMARK OFFICE
CERTIFICATE OF CORRECTION

| | |
|---|---|
| PATENT NO. | : 10,575,907 B2 |
| APPLICATION NO. | : 15/629044 |
| DATED | : March 3, 2020 |
| INVENTOR(S) | : Zvi Dekel et al. |

It is certified that error appears in the above-identified patent and that said Letters Patent is hereby corrected as shown below:

On the Title Page

In Item (72), under "Inventors", in Column 1, Line 1, delete "Zichron Yaakov (IL);" and insert -- Zikhron Ya'akov (IL); --, therefor.

In the Specification

In Column 7, Line 61, delete "an" and insert -- and --, therefor.
In Column 9, Line 14, delete "angles my" and insert -- angles --, therefor.

Signed and Sealed this
Fifteenth Day of August, 2023

Katherine Kelly Vidal
*Director of the United States Patent and Trademark Office*